(12) United States Patent
Isham et al.

(10) Patent No.: US 8,241,317 B2
(45) Date of Patent: *Aug. 14, 2012

(54) MINIMALLY INVASIVE RECTAL BALLOON APPARATUS

(75) Inventors: John Isham, Houston, TX (US); Erik Frija, Albuquerque, NM (US)

(73) Assignee: RadiaDyne LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/748,494

(22) Filed: Mar. 29, 2010

(65) Prior Publication Data

US 2010/0179582 A1   Jul. 15, 2010

Related U.S. Application Data

(63) Continuation of application No. 12/034,470, filed on Feb. 20, 2008, now Pat. No. 8,080,031, which is a continuation-in-part of application No. 11/933,018, filed on Oct. 31, 2007, now abandoned, which is a continuation-in-part of application No. 11/623,702, filed on Jan. 16, 2007, now abandoned.

(51) Int. Cl.
*A61M 29/00* (2006.01)
(52) U.S. Cl. .................. 606/197; 606/192; 606/193
(58) Field of Classification Search .......... 606/190, 606/192, 193, 197
See application file for complete search history.

(56) References Cited

U.S. PATENT DOCUMENTS

| | | | |
|---|---|---|---|
| 3,799,170 A * | 3/1974 | Walsh et al. | ............ 606/193 |
| 4,043,345 A | 8/1977 | Kramann et al. | |
| 4,311,146 A | 1/1982 | Wonder | |
| 4,650,463 A | 3/1987 | LeVeen et al. | |
| 4,784,133 A | 11/1988 | Mackin | |
| 4,994,033 A | 2/1991 | Shockey et al. | |
| 5,116,310 A | 5/1992 | Seder et al. | |
| 5,219,792 A | 6/1993 | Kim et al. | |
| 5,234,454 A | 8/1993 | Bangs | |
| 5,355,087 A * | 10/1994 | Claiborne et al. | ............ 324/322 |

(Continued)

FOREIGN PATENT DOCUMENTS

JP      10-127771 A      5/1998

OTHER PUBLICATIONS

D'Amico, Anthony V. et al., "A Practical Method to Achieve Prostate Gland Immobilization and Target Verification for Daily Treatment," Int. J. Radiation Oncology Biol. Phys., 2001 pp. 1431-1436, vol. 51 No. 5, © 2001 Elsevier Science Inc., U.S.A. (6 pages).

(Continued)

*Primary Examiner* — Ryan Severson
*Assistant Examiner* — Tin Nguyen
(74) *Attorney, Agent, or Firm* — Boulware & Valoir

(57) ABSTRACT

A rectal balloon apparatus has a shaft with a fluid passageway extending therethrough. A balloon is affixed over an end of the shaft such that the fluid passageway communicates with an interior of the balloon. The balloon has a laterally flat surface thereon when inflated. The laterally flat surface of the balloon has a longitudinal groove formed thereon. A valve assembly is affixed to the shaft at an end opposite the balloon. The valve assembly selectively allows a fluid to pass therethrough to move the balloon from a non-inflated condition to an inflated condition. A fluid introducing means is removably attached to the valve assembly to introduce the fluid into the valve assembly.

11 Claims, 4 Drawing Sheets

U.S. PATENT DOCUMENTS

| | | | |
|---|---|---|---|
| 5,360,414 A | 11/1994 | Yarger | |
| 5,433,252 A | 7/1995 | Wolf et al. | |
| 5,512,051 A | 4/1996 | Wang et al. | |
| 5,527,280 A | 6/1996 | Goelz | |
| 5,545,220 A | 8/1996 | Andrews et al. | |
| 5,679,423 A | 10/1997 | Shah | |
| 5,704,913 A | 1/1998 | Abele et al. | |
| 5,792,070 A * | 8/1998 | Kauphusman et al. | 600/549 |
| 5,833,915 A | 11/1998 | Shah | |
| 5,868,776 A | 2/1999 | Wright | |
| 5,879,499 A | 3/1999 | Corvi | |
| 5,924,456 A | 7/1999 | Simon | |
| 5,996,639 A | 12/1999 | Gans et al. | |
| 6,022,313 A | 2/2000 | Ginn et al. | |
| 6,024,753 A | 2/2000 | Claren et al. | |
| 6,102,929 A | 8/2000 | Conway et al. | |
| 6,156,053 A | 12/2000 | Gandhi et al. | |
| 6,249,708 B1 | 6/2001 | Nelson et al. | |
| 6,291,543 B1 | 9/2001 | Shah | |
| 6,352,077 B1 | 3/2002 | Shah | |
| 6,460,541 B1 | 10/2002 | Shah et al. | |
| 6,478,789 B1 | 11/2002 | Spehalski et al. | |
| 6,520,977 B2 | 2/2003 | Piraka | |
| 6,663,646 B1 | 12/2003 | Shah | |
| 6,712,832 B2 | 3/2004 | Shah | |
| 6,733,512 B2 | 5/2004 | McGhan | |
| 6,746,465 B2 | 6/2004 | Diederich et al. | |
| 6,805,662 B2 | 10/2004 | Shah et al. | |
| 6,827,710 B1 | 12/2004 | Mooney et al. | |
| 6,875,193 B1 | 4/2005 | Bonnette et al. | |
| 6,981,980 B2 | 1/2006 | Sampson et al. | |
| 7,112,186 B2 | 9/2006 | Shah | |
| 7,220,252 B2 | 5/2007 | Shah | |
| 7,470,251 B2 | 12/2008 | Shah | |
| 7,976,497 B2 | 7/2011 | Shah et al. | |
| 8,080,031 B2 * | 12/2011 | Isham | 606/197 |
| 2001/0027307 A1 * | 10/2001 | Dubrul et al. | 604/508 |
| 2003/0028097 A1 * | 2/2003 | D'Amico et al. | 600/427 |
| 2003/0088209 A1 | 5/2003 | Chiu et al. | |
| 2005/0004592 A1 * | 1/2005 | Criscuolo | 606/190 |
| 2005/0222329 A1 | 10/2005 | Shah | |
| 2005/0267509 A1 * | 12/2005 | Davis, Jr. | 606/193 |
| 2006/0094923 A1 | 5/2006 | Mate | |
| 2006/0212064 A1 | 9/2006 | Shah | |
| 2007/0212559 A1 | 9/2007 | Shah | |
| 2007/0239110 A1 | 10/2007 | Shah | |
| 2007/0299463 A1 | 12/2007 | Shah | |
| 2008/0119785 A1 * | 5/2008 | Ramsey et al. | 604/98.01 |
| 2008/0188802 A1 | 8/2008 | Shah | |
| 2008/0262449 A1 | 10/2008 | Shah et al. | |
| 2008/0262450 A1 | 10/2008 | Shah et al. | |
| 2009/0082724 A1 | 3/2009 | Shah et al. | |

OTHER PUBLICATIONS

D'Amico, Anthony V. et al., "A Prospective Evaluation of Rectal Bleeding After Dose-Escalated Three-Dimensional Conformal Radiation Therapy Using an Intrarectal Balloon for Prostate Gland Localization and Immobilization," 2005, Journal Urology, pp. 780-784, vol. 67, No. 4, © 2006 Elsevier Inc. (5 pages).

Little, Darren J. et al., Use of Portal Images and BAT Ultrasonography to Measure Setup Error and Organ Motion for Prostate IMRT: Implications for Treatment Margins, Int'l J. Radiation Oncology Biol. Phys., 2003, pp. 1218-1224, vol. 56, No. 56, No. 5 © 2003 Elsevier Inc. (7 pages).

McGary, John E. et al., Prostate Immobilization Using a Rectal Balloon, Journal of Applied Clinical Medical Physics, 2002, pp. 6-11, vol. 3, No. 1, © 2002 Am. Coll. Med. Phys. (6 pages).

Patel, Rakesh R. et al., "Rectal Dose Sparing with a Balloon Catheter and Ultrasound Localization in Conformal Radiation Therapy for Prostate Cancer," Radiotherapy & Oncology Journal of the European Society for Therapeutic Radiology and Oncology, 2003, pp. 285-294, vol. 67, © 2003 Elsevier Science Ireland Ltd. (10 pages).

Van Lin, Emile N. J. TH. et al., "Rectal Wall Sparing Effect of Three Different Endorectal Balloons in 3D Conformal and IMRT Prostate Radiotherapy," Int'l J. Radiation Oncology Biol. Phys., 2005, pp. 565-576, vol. 63, No. 2 © 2005 Elsevier, Inc. (12 pages).

Poli, M. Esmeralda Ramos et al., An Assessment of PTV Margin Definitions for Patients Undergoing Conformal 3D External Beam Radiation Therapy for Prostate Cancer Based on an Analysis of 10,327 Pretreatment Daily Ultrasound Localizations, Int. J. Radiation Oncology Biol. Phys., 2007, pp. 1430-1437, vol. 67, No. 5, © Elsevier Inc. (8 pages).

Pollack, Alan et al., "Prostate Cancer Radiation Dose Response: Results of the M.D. Anderson Phase III Randomized Trial," Int. J. of Radiation Oncology Biol. Phys., 2002, pp. 1097-1105, vol. 53, No. 5, © 2002 Elsevier Science Inc. (9 pages).

Storey, Mark R. et al., "Complications from Radiotherapy Dose Escalation in Prostate Cancer: Preliminary Results of a Randomized Trial," Int J. Radiation Oncology Biol. Phys., 2000, pp. 635-642, vol. 48, No. 3, © 2000 Elsevier Science Inc. (8 pages).

Van Lin, Emile N.J. TH. et al., "Reduced Late Rectal Mucosal Changes After Prostate Three-Dimensional Conformal Radiotherapy with Endorectal Balloon as Observed in Repeated Endoscopy," Int. J. Radiation Oncology Biol. Phys., 2007, pp. 799-811, vol. 67, No. 3, © 2007 Elsevier Inc. (13 pages).

Wang, Zhou et al., "The Effect of Positional Realignment on Dose Delivery to the Prostate and Organs-at-Risk for 3DCRT," Medical Dosimetry, 2007, pp. 1-6, vol. 32, No. 1, © 2007 American Association of Medical Dosimetry (6 pages).

Zietman, A. L. et al., "A Randomized Trial Comparing Conventional Dose (70.2 GyE) and High-Dose (79.2 GyE) Conformal Radiation in Early Stage Adenocarcinoma of the Prostate; Results of an Interim Analysis of RROG 45-09" Int. J. Radiation Oncology Biol. Phys., 2004, pp. S131-S132, vol. 60, No. 1, Supp. 2004, © 2004 Elsevier B. V. (2 pages).

*Polyzen, Inc.* v. *RadiaDyne, L.L.C.*, U.S. District Court for the Eastern District of North Carolina, Civil Action No. 5:11-cv-00662.

* cited by examiner

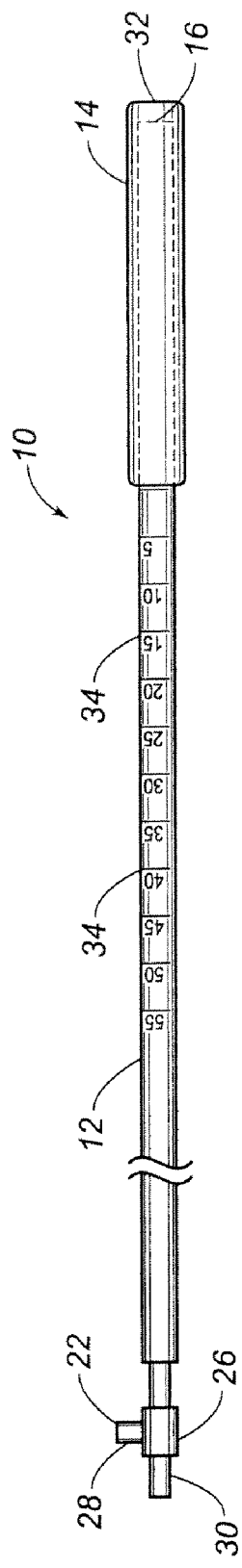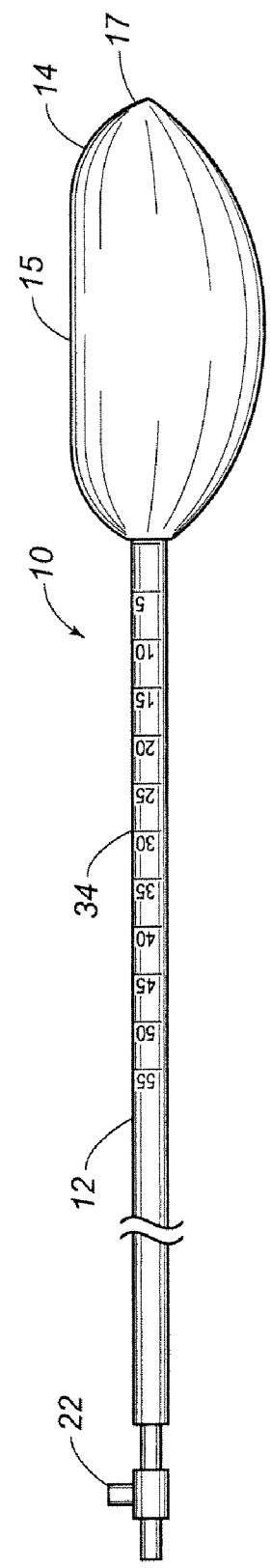

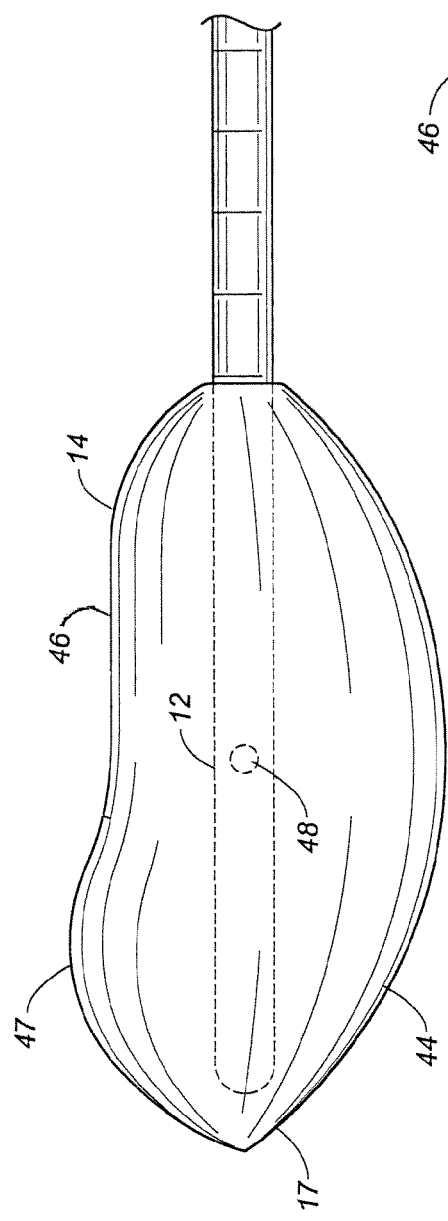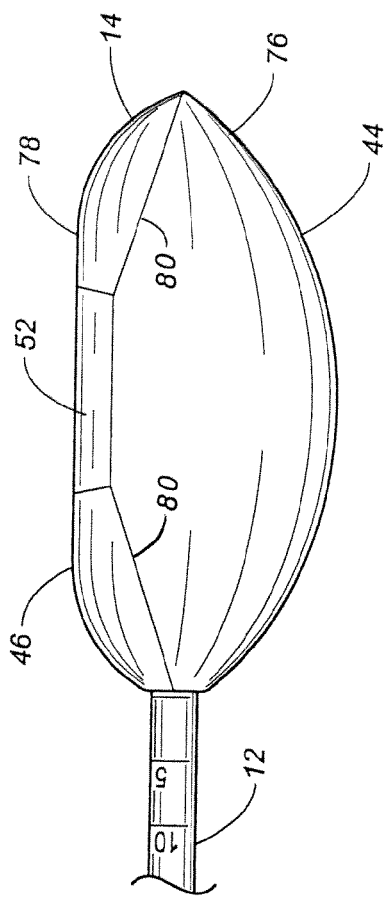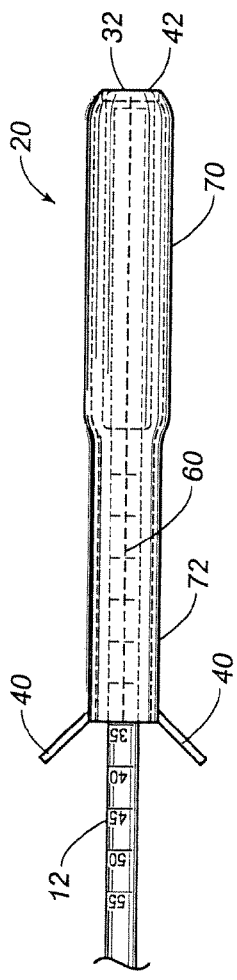

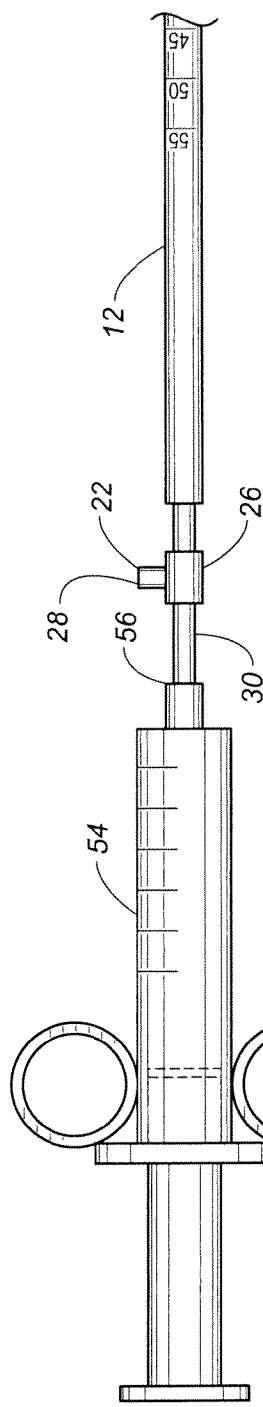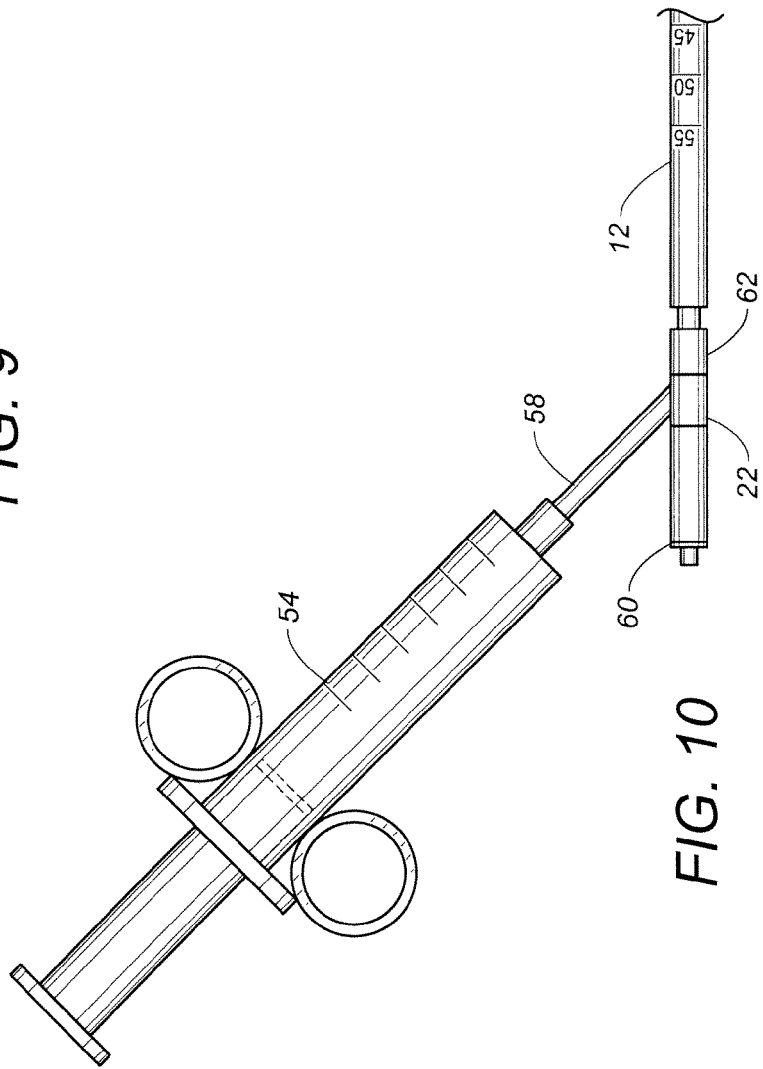
FIG. 9
FIG. 10

MINIMALLY INVASIVE RECTAL BALLOON APPARATUS

CROSS-REFERENCE TO RELATED APPLICATIONS

This application is a continuation of U.S. application Ser. No. 12/034,470, filed on Feb. 20, 2008, now patented as U.S. Pat. No. 8,080,031, which is a continuation-in-part of U.S. application Ser. No. 11/933,018 filed on Oct. 31, 2007, now abandoned, which is a continuation-in-part of U.S. application Ser. No. 11/623,702 filed on Jan. 16, 2007, now abandoned, which are all hereby incorporated by reference for all purposes in their entirety.

STATEMENT REGARDING FEDERALLY SPONSORED RESEARCH OR DEVELOPMENT

N/A

NAMES OF PARTIES TO A JOINT RESEARCH AGREEMENT

N/A

REFERENCE TO AN APPENDIX SUBMITTED ON COMPACT DISC

N/A

BACKGROUND OF THE INVENTION

1. Field of the Invention

The invention relates to rectal balloons that are used for immobilizing the region surrounding the prostate.

2. Description of the Related Art

Treatment of prostate cancer using radiation therapy is difficult due to the prostate's position near radiation-sensitive tissues, and is further complicated by prostate motion. Adenocarcinoma of the prostate commonly occurs in the posterior portion of the prostate gland which is in very close proximity to the rectal wall. To plan external beam radiation treatment, urethrograms, CT scans and magnetic resonance imaging (MRI) have all been used to visually localize the prostate, as well as the normal critical structures in the surrounding area.

U.S. Pat. No. 5,476,095, issued on Dec. 19, 1995 to Schnall et al., describes an insertable pickup probe for use in providing diagnostic MRI images. The pickup probe in its preferred embodiment is for use in imaging the male prostate and comprises an elongated shaft supporting an inflatable patient interface balloon at its distal end. The interface balloon comprises an inner balloon and an outer balloon, between which a receiving coil is positioned. A lumen for air supply is provided in the shaft for expanding the inner balloon against the outer balloon to place the receiving coil in close proximity to the area of interest in order to provide MRI images.

Typically, the planning of radiation therapy for the treatment of prostate cancer involves the patient undergoing a CT-based simulation scan of the pelvis to determine the location of the prostate gland. In the simulation phase, the patient is placed on CT equipment that is preferably similar to the radiation treatment equipment (except that it does not generate the high energy radiation beam). The simulation equipment is positioned to simulate the delivery of the sequence of treatment beams prescribed by the treating oncologist. Normally, during the simulation procedure, CT images are acquired. These CT images allow the oncologist to locate the position of the tumor and help to facilitate the composition of a radiation treatment plan. This treatment plan delineates the positions of the radiation equipment components for delivery of the treatment beams.

During the actual treatment phase, the patient is placed in the same position on the treatment equipment as in the simulation scans. Radiation-emitting devices are generally known and used for radiation therapy in the treatment of patients. Typically, a radiation therapy device includes a gantry, which can be swiveled around a horizontal axis of rotation in the course of a therapeutic treatment. A linear accelerator is located in the gantry for generating a high-energy radiation beam for therapy. During treatment, the radiation beam is provided by this equipment and is delivered to the patient at the precise location as delineated by the physician during simulation. A further feature of radiation therapy involves portal images, which are commonly used in radiation therapy to verify and record the patient tumor location. Portal images include manual (film) and electronic images (EPI) taken before and/or after the treatment.

During external beam radiation therapy, radiation is directed to the target prostate which is near the rectal wall. A misdirected radiation beam may perforate the rectal wall causing radiation proctitus (rectal bleeding). This toxicity is related to the total radiation dose prescribed and the volume of the anterior rectal wall receiving a high radiation dose. A major factor limiting radiation oncologists' attempts to reduce the volume of the anterior rectal wall receiving a high radiation dose is the position of the prostate gland as well as the intrinsic motion up to 5 mm in the anterior to posterior direction caused by rectal peristalsis. Accordingly, oncologists generally will add a margin to the radiation field in order to ensure that the entire prostate gland receives the prescription dose. This margin is typically on the order of 5 to 15 mm. As a consequence, lower doses of radiation may need to be used so as not to overexpose radiation sensitive structures. However, this may lead to inadequate radiation treatment and a higher probability of local cancer recurrence.

U.S. Patent Publication No. 2003/0028097, published on Feb. 6, 2003 to D'Amico et al., describes an immobilizer probe system and method. This system has an insertable probe for immobilizing a region of interest during staging and radiation therapy thereof. In particular, this device uses a balloon having a rectangular cross section connected to a shaft. The shaft extends to an end of the balloon so as to allow fluid flow through an interior of the shaft and into the balloon so as to selectively inflate the balloon once the balloon is installed into the rectal cavity. The balloon, shaft and handle are bonded together so that they move radially as a single unit when torque is applied. A syringe is provided which connects the shaft and serves as an air pump to deliver a volume-limited amount of air to the air lumen of the shaft to the balloon. A stop cock is provided to maintain the air within the balloon.

One of the problems with the subject of U.S. Patent Publication No. 2003/0028097 is the discomfort associated installing the rectal balloon within the rectal cavity. In particular, a relatively sturdy and wide diameter shaft is connected to a relatively large thick-walled balloon. Because the balloon is not supported by anything other than by the shaft, the balloon is formed of a relatively rugged and thick material. Because of the relatively large size of the shaft and the thick material of the rectangular-cross section balloon, the installation of the rectal balloon creates a large amount of discomfort for a patient. It is often difficult for the medical personnel to know exactly how far within the rectum the balloon has been installed. It is difficult to achieve a standardized and fixed position of the balloon during each and every use. The medical personnel must generally approximate the desired position of the balloon within the rectal cavity. As such, a need has developed whereby the rectal balloon can be formed of a minimal diameter shaft and of a balloon of relatively thin material.

When the rectal balloon of U.S. Patent Publication No. 2003/0028097 is in an inflated condition, the outer surface is generally round. As such, the prostate will tend to balance on the curved surface rather than properly seating thereon. Since seating is important for proper use, this device requires that the physician approximate a seated position rather than providing any feedback of the seated position. When the balloon is in a curved inflated condition, the prostate will have a tendency to slide to one side of the balloon. As such, a need developed to provide a rectal balloon that retains the prostate in a proper seated position when the balloon is in a fully inflated condition.

It is an object of the invention to provide a rectal balloon apparatus which is easy to use and easy to install.

It is another object of the invention to provide a rectal balloon apparatus whereby the position of the balloon can be easily ascertained by medical personnel.

It is a further object of the invention to provide a rectal balloon apparatus which maximizes the comfort to the patient.

It is a further object of the invention to provide a rectal balloon apparatus which has better holding stability when inflated.

It is a further object of the invention to provide a rectal balloon apparatus which has a flexible shaft.

It is another object of the invention to provide a rectal balloon apparatus which can be inflated to several configurations for different medical purposes.

It is another object of the invention to provide a rectal balloon apparatus which enhances the ability to properly seat the prostate on a flat surface of the rectal balloon.

It is a further object of the invention to provide a rectal balloon apparatus which avoids potential allergic reactions.

It is still a further object of the invention to provide a rectal balloon apparatus which is easy to manufacture and relatively inexpensive.

These and other objects and advantages of the invention will become apparent from a reading of the attached specification and appended claims.

BRIEF SUMMARY OF THE INVENTION

The invention is a rectal balloon apparatus that comprises a shaft having a fluid passageway extending therethrough and a balloon affixed over an end of the shaft such that the fluid passageway communicates with an interior of the balloon. The balloon is movable from a non-inflated condition to a first inflated condition. The balloon has a laterally flat surface when in the first inflated condition. The balloon is movable from the first inflated condition to a second inflated condition. In the second inflated condition, the balloon has both a laterally flat surface and a bulbous portion.

In the invention, a groove is formed in the laterally flat surface. The groove extends longitudinally along a portion of the laterally flat surface. The groove has a generally rectangular shape. The balloon has a generally V-shaped end portion. The shaft is made of a flexible material. There is a valve means affixed to the shaft at an end opposite the balloon. The valve means is for selectively allowing a fluid to pass through the shaft and to the balloon so as to move the balloon from a non-inflated condition to an inflated condition. The valve means has a port thereon. A fluid introducing means is removably connected to the port and can move the balloon from a non-inflated condition to an inflated condition. The non-inflated condition can be a vacuum such that the balloon resides tightly over the shaft. The first inflated condition is reached when the balloon has approximately 100 cc of fluid therein. The second inflated condition is reached when the balloon has approximately 140 cc of fluid therein.

In the invention, there is a sleeve slidably affixed over the shaft and movable between a first position overlying the balloon and a second position away from the balloon. The sleeve has a first portion frangibly joined to a second portion. The first portion has a tab extending outwardly from an end of the first portion. The second portion also has a tab extending outwardly from the second portion.

The balloon of the invention is formed of a plurality of layers bonded together. The balloon has a groove formed along a surface thereof. The plurality of layers has a top layer, a middle layer, and a bottom layer. The top layer and the middle layer are joined along the groove.

The invention is also a rectal balloon apparatus that comprises a shaft having a fluid passageway extending therethrough and a balloon affixed over an end of the shaft such that the fluid passageway communicates with an interior of the balloon. The balloon is movable from a non-inflated condition to a first inflated condition. The balloon has a laterally flat surface when in the first inflated condition. The balloon is tightly juxtaposed over the shaft when the balloon is in the non-inflated condition. The balloon is movable from the first inflated condition to a second inflated condition. In the second inflated condition, the balloon has both a laterally flat surface and a bulbous portion. A groove is formed in the laterally flat surface. There is a valve means affixed to the shaft at an end opposite the balloon. The valve means is for selectively allowing a fluid to pass through the shaft and to the balloon so as to move the balloon from a non-inflated condition to an inflated condition.

BRIEF DESCRIPTION OF THE DRAWINGS

A better understanding of the invention can be obtained with the following detailed descriptions of the various disclosed embodiments in the drawings, which are given by way of illustration only, and thus are not limiting the invention, and wherein:

FIG. 1 is a side elevational view, partially transparent, which shows the rectal balloon apparatus in an uninflated condition.

FIG. 2 is a side elevational view of the rectal balloon apparatus in the first inflated condition.

FIG. 6 is a side view, partially transparent, of the balloon of the rectal balloon apparatus in the second inflated condition.

FIG. 7 is an isolated view of the sleeve as used in the rectal balloon apparatus.

FIG. 8 is a cross-sectional side view of the balloon of the rectal balloon apparatus showing the plurality of layers which form the balloon.

FIG. 9 is an isolated view showing the valve assembly of the rectal balloon apparatus in an aligned configuration.

FIG. 10 is an isolated view showing the valve assembly of the rectal balloon apparatus in an angled configuration.

DETAILED DESCRIPTION OF THE INVENTION

Figure 3:
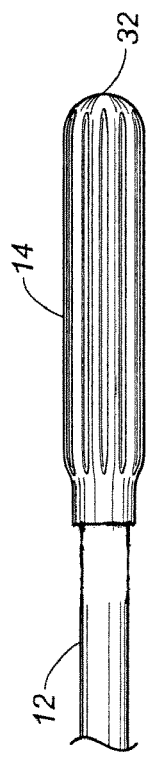
FIG. 3 is an isolated view showing the compact folding of the balloon over the end of the shaft.

Referring to FIG. 1, there is shown the rectal balloon apparatus 10 in accordance with the preferred embodiment. The rectal balloon apparatus 10 includes a shaft 12 having a fluid passageway extending therethrough. A balloon 14 is affixed over the end 16 of the shaft 12. The balloon 14 is shown in an uninflated condition. The fluid passageway of the shaft 12 can communicate with the interior of the balloon 14.

The shaft 12 is a generally longitudinal shaft which has the fluid passageway extending through the center thereof. The shaft 12 is made of a flexible material. A valve assembly 22 is affixed to the shaft 12 opposite the balloon 14. The valve assembly 22 can have a variety of configurations. FIG. 1 illustrates the valve assembly 22 as an inline valve assembly configuration. The valve assembly 22 may also be an angled valve assembly configuration. The valve assembly 22 includes a stop cock 26. A valve 28 facilitates the ability of the stop cock 26 to open and close so as to selectively allow the fluid to pass into the shaft 12. A port 30 allows the valve assembly 22 to be connected to a supply of the fluid. When the stop cock 26 is opened by the rotation of the valve 28, the fluid will flow through the valve assembly 22, through the interior passageway of the shaft 12, and into the interior of the balloon 14. The valve 28 can then be closed so as to maintain the inflated configuration of the balloon 14. When the procedure is finished and the fluid needs to be removed from the balloon 14, the valve 28 of stop cock 26 can then be opened so as to allow for the release of fluid therethrough.

The opposite end 16 of the shaft 12 contacts the end 32 of the balloon 14. The end 16 is suitably curved or dome-shaped so as to allow the shaft 12 to facilitate the introduction of the balloon 14 into the rectal cavity. The shaft 12 has indicia 34 formed therealong. It can be seen that the indicia 34 has numerical references associated therewith. These numerical references are indicative of the distance that the balloon 14 has been inserted into the rectum. As such, the indicia 34 provide a clear indication to the medical personnel of the desired location of the rectal balloon 14.

FIG. 2 illustrates the apparatus 10 after the apparatus has been installed within the rectum. The fluid can be introduced through the valve assembly 22 and through the interior passageway of the shaft 12 so as to inflate the balloon 14. The balloon 14 has a seating area 15 so that the prostate can be properly positioned thereon. The balloon 14 has a head portion 17 adjacent the tip of the balloon 14 opposite the shaft 12. When the balloon 14 is installed and inflated, the prostate will reside on the flat surface 15 in a seated position. The head portion 17 will abut the tip of the prostate. After the procedure has been completed, the balloon 14 can be deflated and easily pulled outwardly of the rectum in its deflated condition.

FIG. 3 shows that the balloon 14 is neatly folded and compressed over the outer diameter of the shaft 12. The shaft 12 will have a rounded end abutting the end 32 of the balloon 14. As such, a comfortable rounded profile is provided at this end 32. The end 32 of the balloon 14 is sealed over the outer diameter of the shaft 12. The balloon 14 is pre-vacuumed during production to produce a minimal profile during use.

Figure 4:
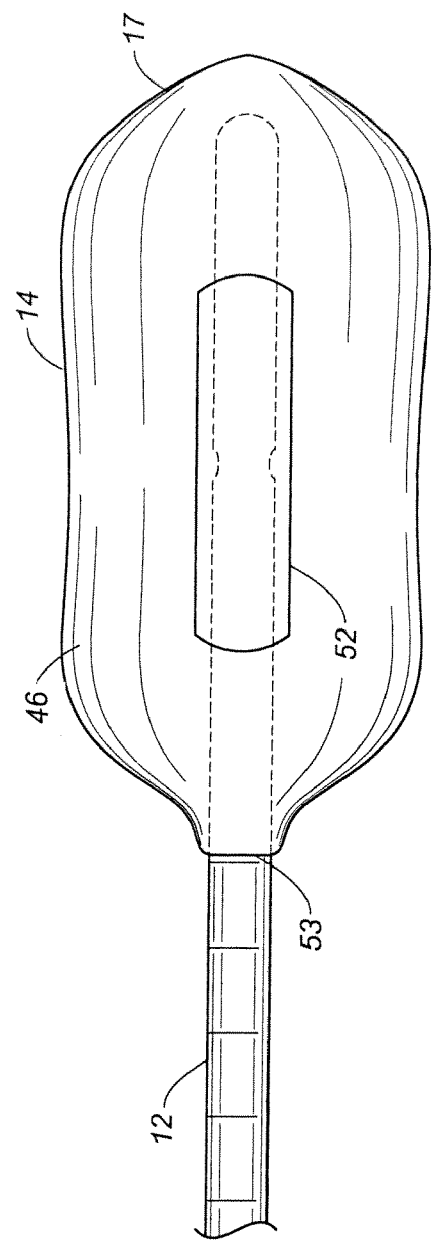
FIG. 4 is a top view of the inflated balloon as used in the rectal balloon apparatus.

FIG. 4 is a top view of the balloon 14 from the side of the balloon 14 which engages with the prostate. Central seating area 46 is shown as having a groove 52 formed thereon. The groove 52 is generally rectangularly-shaped and engages with the tip of the prostate and reduces lateral motion. The central seating area 46 and the groove 52 enhance the holding stability of the balloon 14 of the present invention. In FIG. 4, it can also be seen that head portion 17 of the balloon 14 is generally V-shaped. This shape makes insertion of the balloon 14 into the rectum easier for medical personnel and more comfortable for the patient. The balloon 14 has a thermally welded bond 53 connecting it to the shaft 12.

Figure 5:
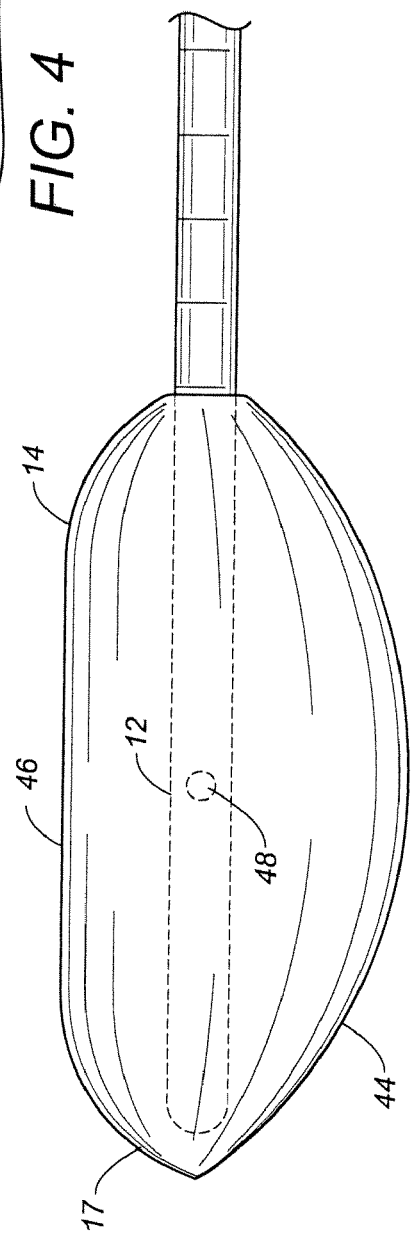
FIG. 5 is a side view, partially transparent, of the balloon of the rectal balloon apparatus in the first inflated condition.

FIG. 5 is an isolated view of the balloon 14 as inflated to a first inflated condition. In this first condition, the balloon 14 has a central seating portion 46, a head portion 17 and a bottom portion 44. The central seating area 46 has a lateral flatness when inflated for the prostate to rest upon. The first inflated condition is formed when approximately 100 cc of fluid are introduced into the balloon 14. The lateral flatness of the seating area 46 will prevent the prostate from sliding to one side or the other. The bottom portion 44 is rounded and contacts the rectal wall. The head portion 17 is generally V-shaped so as to facilitate easier insertion of the balloon 14. The material of the balloon 14 is formed of a non-latex material so as to avoid allergic reactions. The shaft 12 is shown extending into the interior of the balloon 12. A hole 48 is formed in the shaft 12 through which the balloon 14 is filled with fluid. The hole 48 is fowled generally centrally within the balloon 14.

FIG. 6 is an isolated view of the balloon 14 as inflated to a second inflated condition. In the second inflated condition, the balloon 14 has a bulbous portion 47 formed adjacent to the head portion 17. The balloon also has a laterally flat seating portion 46. The bulbous portion 47 can be utilized in certain conditions to better isolate the prostate. Generally, the bulbous portion 47 will be formed when at least 140 cc of fluid are introduced into the balloon 14.

FIG. 7 is an isolated view of the sleeve 20. The sleeve 20 consists of a first portion 70 and a second portion 72. Importantly, in FIG. 7, it can be seen that the sleeve 20 has a frangible seal 60 extending longitudinally therealong joining first portion 70 and second portion 72. The frangible seal 60 is arranged such that when the sleeve 20 is pulled toward the handle 22, proper pulling forces can cause the sleeve 20 to split longitudinally therealong so that the sleeve 20 can be permanently removed from the shaft 12. The sleeve 20 has tabs 40 attached to first portion 70 and second portion 72 at an end opposite the balloon 14 to be used when pulling the sleeve 20. The sleeve 20 also has an aperture 42 formed at an end opposite to the tabs 40. The aperture 42 allows the end 32 of the balloon 14 to extend slightly outwardly therefrom. As such, the end 42 will create a smooth contour, in combination with the end 32, so as to facilitate the ease of insertion of the apparatus 10.

FIG. 8 cross-sectional side view of the balloon 14 showing the plurality of layers which form the balloon 14. A bottom layer 76 forms the bottom portion 44 of the balloon 14. A top layer 78 forms the upper portion, including central sealing area 46 and the groove 52, of the balloon 14. A middle layer 80 extends between the bottom layer 76 and the top layer 78. The middle layer 80 is connected to the top layer 78 at the groove 52.

FIG. 9 shows an isolated view of the shaft 12 of the rectal balloon apparatus 10 at an end opposite the balloon 14. The valve assembly 22 is shown in an online configuration. The valve assembly 22 is connected at one end to the shaft 12 and at the opposite end to a fluid introducing device 54. In this case, the fluid introducing device 54 is a syringe. The syringe 54 serves as a removable handle for the rectal balloon apparatus 10. An end portion 56 of the syringe 54 is removably connected to the port 30 of the valve assembly 22. When the valve 28 and the stop cock 26 are in an open position, fluid can travel from the syringe 54 into the shaft 12 and to the balloon 14. With the balloon 14 inflated, the valve assembly may be closed and the syringe 54 removed. The syringe 54 can be reconnected to the valve assembly 22 prior to removal of the balloon 14 from the rectum to aid in removing the fluid from the balloon 14.

FIG. 10 also shows an isolated view of the shaft 12 of the rectal balloon apparatus 10 at an end opposite the balloon 14. Here, the valve assembly 22 is shown in an angled configuration. The angled configuration may be utilized to give the apparatus a smaller profile. The valve assembly 22 in the angled configuration is connected at one end to the shaft 12 and is closed at an opposite end 60. A port 58 extends at approximately a 45° angle relative to the shaft 12 in a direction away from the balloon 14. A syringe 54 is removably attached to the connector 58. A valve 62 is located on the valve assembly 22 in a position between the connector 58 and the shaft 12. With the valve 62 in an open position, fluid may be passed into or out of the shaft 12 and the balloon 14.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

We claim:

1. A prostate immobilizing rectal balloon, said rectal balloon comprising:
   a. a flexible shaft having a fluid passageway extending therethrough and having a distal end and a proximal end,
   b. one balloon having an upper portion, a bottom portion, a distal end near said distal end of said shaft and a proximal end that is affixed to said shaft, such that said fluid passageway communicates with an interior of said balloon,
   c. wherein said balloon comprises a top layer, a middle layer and a bottom layer, said layers bonded together along their edges to form said balloon,
   d. wherein said middle layer is connected to said top layer at a groove,
   e. wherein said balloon has a non-inflated position,
   f. wherein said balloon has an inflated position wherein said upper portion is generally laterally flat and said bottom portion is rounded, said groove forming a central seating area that is configured to engage with a prostate when inflated.

2. The prostate immobilizing rectal balloon of claim 1, said groove extending centrally longitudinally along said upper portion.

3. The prostate immobilizing rectal balloon of claim 1, said groove having a generally rectangular shape.

4. The prostate immobilizing rectal balloon of claim 1, wherein said balloon comprises a non-latex material.

5. The prostate immobilizing rectal balloon of claim 1, further comprising a sleeve slidably affixed over said shaft and not attached to said balloon and being movable between a first position overlying said balloon and a second position away from said balloon.

6. The prostate immobilizing rectal balloon of claim 1, said sleeve having a first portion frangibly joined to a second portion, said first portion having a tab extending outwardly from one end thereof, said second portion having a tab extending outwardly from one end thereof.

7. The prostate immobilizing rectal balloon of claim 1, further comprising a valve means affixed to said shaft at said proximal end, said valve means for selectively allowing a fluid to pass through said shaft to said balloon so as to move said balloon from said non-inflated condition to said first inflated condition.

8. The prostate immobilizing rectal balloon of claim 7, said valve means having a port thereon.

9. The prostate immobilizing rectal balloon of claim 8, further comprising a fluid introducing means releasably connected to said port for introducing fluid into an interior of said balloon so as to move said balloon from said non-inflated condition to said inflated condition.

10. The prostate immobilizing rectal balloon of claim 1, said non-inflated condition being a vacuum such that said balloon resides tightly over said shaft.

11. A method of treating a prostate, comprising inserting a prostate immobilizing rectal balloon into a rectum of a patient, said rectal balloon comprising:
   a flexible shaft having a fluid passageway extending therethrough and having a distal end and a proximal end,
   a balloon having an upper portion, a bottom portion, a distal end near said distal end of said shaft and a proximal end that is affixed to said shaft, such that said fluid passageway communicates with an interior of said balloon,
   wherein said balloon comprises a top layer, a middle layer and a bottom layer, said layers bonded together along their edges to form said balloon,
   wherein said middle layer is connected to said top layer at a groove,
   wherein said balloon has a non-inflated position,
   wherein said balloon has an inflated position wherein said upper portion is generally laterally flat and said bottom portion is rounded, said groove forming a central seating area that is configured to engage with a prostate when inflated;
   and inflating said balloon such that said prostate engages with said groove.

* * * * *

UNITED STATES PATENT AND TRADEMARK OFFICE
CERTIFICATE OF CORRECTION

| | | |
|---|---|---|
| PATENT NO. | : 8,241,317 B2 | Page 1 of 1 |
| APPLICATION NO. | : 12/748494 | |
| DATED | : August 14, 2012 | |
| INVENTOR(S) | : John Isham et al. | |

It is certified that error appears in the above-identified patent and that said Letters Patent is hereby corrected as shown below:

In column 8, line 6, the '1' should be replaced with a '5' such that claim 6 reads as "The prostate immobilizing rectal balloon of claim 5, said sleeve having a first portion frangibly joined to a second portion, said first portion having a tab extending outwardly from one end thereof, said second portion having a tab extending outwardly from one end thereof."

Signed and Sealed this
Eighth Day of January, 2013

David J. Kappos
*Director of the United States Patent and Trademark Office*